United States Patent [19]

Gude et al.

[11] Patent Number: 4,855,488

[45] Date of Patent: Aug. 8, 1989

[54] PROCESS FOR THE PREPARATION OF DICYCLOPENTENOL ESTERS

[75] Inventors: Fritz Gude, Herne; Hans Bellut, Duelmen, both of Fed. Rep. of Germany

[73] Assignee: Huels Aktinegesellschaft, Marl, Fed. Rep. of Germany

[21] Appl. No.: 198,749

[22] Filed: May 25, 1988

[30] Foreign Application Priority Data

Jul. 18, 1987 [DE] Fed. Rep. of Germany ....... 3723891

[51] Int. Cl.$^4$ .............................................. C07C 67/02
[52] U.S. Cl. ..................................... 560/249; 560/256; 560/107; 560/8
[58] Field of Search ......................... 560/249, 256, 107

[56] References Cited

U.S. PATENT DOCUMENTS

| | | | |
|---|---|---|---|
| 2,394,582 | 1/1946 | Bruson | 560/256 |
| 2,395,452 | 2/1946 | Bruson | 560/256 |
| 2,411,516 | 11/1946 | Bruson | 560/256 |
| 2,414,089 | 1/1947 | Bruson | 560/256 |
| 2,817,673 | 12/1957 | Roelen et al. | 560/256 |
| 3,417,132 | 12/1968 | Dunkel | 560/256 |
| 3,445,508 | 5/1969 | Dunkel | 560/256 |
| 3,489,792 | 1/1970 | Greenbaum | 560/256 |

Primary Examiner—Paul J. Killos
Attorney, Agent, or Firm—Oblon, Spivak, McClelland, Maier & Neustadt

[57] ABSTRACT

A process for the preparation of a dicyclopentenol ester of the formula:

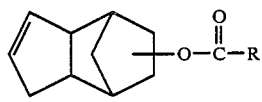

wherein R is a $C_{1-12}$ alkyl group, a $C_{6-12}$ aryl group or a $C_{6-12}$ substituted aryl group is disclosed. In this process dicyclopentadiene is reacted with an organic carboxylic acid of the formula:

R—CO—OH in the presence of a catalyst. The catalyst comprises a readily volatile addition compound of $BF_3$.

8 Claims, No Drawings

PROCESS FOR THE PREPARATION OF DICYCLOPENTENOL ESTERS

BACKGROUND OF THE INVENTION

1. Field of the Invention

The present invention relates to processes for the preparation of dicyclopentenol esters.

2. Discussion of the Background

Various processes are known for the preparation of dicyclopentenol esters having the following formula:

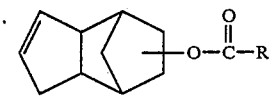

wherein R is a $C_{1-12}$ alkyl group, an aryl group, or a substituted aryl group. In general, all these processes start with the same raw materials: cyclopentadiene and an organic acid. They all require however expensive and time-consuming processing steps.

Processes which use solid catalysts require a filtration operation. Processes using liquid catalysts require a neutralization and an aqueous extraction operation.

In both of these processes, the catalyst system used is completely lost. This causes, among other problems, the problem of disposal and work-up. Due to these additional processing steps, the cost of the end product becomes very high.

In all existing processes, prior to product work-up, the catalyst systems are either destroyed or removed from the reaction mixture to (1) prevent the ester from splitting back to the starting materials, and (2) to prevent the reaction product from further resinifying.

It is known that of various kinds of acids, such as sulfuric acid, peracetic acid, or organic sulfonic acids, boron fluoride and boron fluoride phosphoric acids can also be used as esterification catalysts (U.S. Pat No. 2,457,157). However boron fluoride has the undesirable property of catalyzing the oligomerization of olefinic compounds (see F. H. S. Booth and D. R. Martin in Boron Trifluoride and its Derivatives, John Wiley and Sons, Inc., 1949). In the case of dicyclopentenol ester, oligomerization leads to increased resin formation.

In view of the usefulness of dicyclopentenol esters, there is thus a strongly need for a more efficient process for producing these materials.

SUMMARY OF THE INVENTION

Accordingly, it is an object of the present invention to provide an economic process for the preparation of dicyclopentenol esters.

It is another object of this invention to provide an effective process for the preparation of dicyclopentenol esters.

The inventors have now discovered a process which satisfies all of these objects, and other objects which will become apparent from the description of the invention given hereinbelow. In this process for the preparation of dicyclopentenol esters of the general formula:

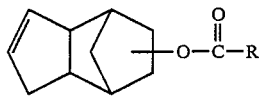

wherein: R is $C_{1-12}$ alkyl, $C_{6-12}$ aryl, or $C_{6-12}$ aryl substituted by at least one member selected from the group consisting of halogen atoms (i.e. fluoro, chloro and bromo) and $C_{1-3}$ alkyls, preferably a chloro or a $C_{1-3}$ alkyl group.

In this process dicyclopentadiene is reacted with the corresponding organic carboxylic acid, R—COOH, in the presence of a Lewis acid catalyst. At least one readily volatile addition compound of $BF_3$ is used as the catalyst.

DETAILED DESCRIPTION OF THE PREFERRED EMBODIMENTS

The present invention relates to a process for the preparation of dicyclopentenol esters from dicyclopentadiene and organic carboxylic acids under the influence of acidic Lewis catalysts.

The reaction and isolation of the product that is described in detail below occurs in a one pot process. No additional time-consuming washing or filtering steps are needed.

Surprisingly, it was now found that the lighter volatile addition compounds of boron fluoride, such as $BF_3$-acetic acid, $BF_3$-propionic acid, $BF_3$-methyl ether, $BF_3$-ethyl ether, $BF_3$-$C_{1-3}$-alcohols, such as $BF_3$ ethanol and the like, actually catalyze the addition of carboxylic acids to olefins, as for example on dicyclopentadiene. Yet when maintaining favorable concentrations, they do not noticeably promote resinification. Therefore, $BF_3$ addition compounds are excellent as auxiliary means for the described addition reaction of carboxylic acids at dicyclopentadiene.

Thus the object of the invention is a process for the preparation of dicyclopentenol esters of the general formula:

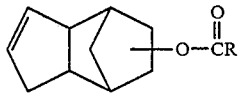

from dicyclopentadiene and the corresponding organic carboxylic acids, in the presence of Lewis acid catalysts. The process is characterized by the fact that at least one readily volatile addition compound of $BF_3$ is added as the catalyst.

The aryl compounds can be for example phenyl-, toluyl, chloro-phenyl, naphthyl-compounds, etc.

The destruction or separate cleavage of the catalyst prior to work-up is superfluous, since during distilling purification it can be readily isolated as a separate fraction and used again. Return-spliting of the formed ester can be omitted under the applied conditions. In this manner a cost-efficient, environmentally safe process for preparing dicyclopentenol esters is possible.

In order to prepare the desired dicyclopentenol ester, commercial dicyclopentadiene is mixed without pretreatment with one to five times the quantity of carboxylic acid, 0.1 to 15% with respect to dicyclopentadiene, preferably however 0.5 to 2%, of a $BF_3$-addition compound is added. The reaction mixture obtained is heated to 100 to 160° C., preferably boiled under reflux, for about ¼ to 2 hours until the reaction has ended.

Thereafter, the reaction mixture is distilled immediately under a vacuum. The first distillate, the carboxylic acid excess and BF₃-addition compounds, can be used for a following batch following replacement of consumed or lost quantities. The ester, which passes over as the main fraction, is led over a washing column of marble or activated charcoal to bind any traces of free acid that might still be present, residues of the catalyst and small oligomeric components. The product obtained has the required specification. The cyclopentenol esters are useful as perfumes.

Common austenite steels, for example of the V4A type, are suitable as a container material for those parts of the apparatus with a thermal load. The achievable yield ranges from 80 to 85%, with respect to the added pure dicyclopentadiene. Another 5 to 10% can be obtained as tailings by more drastic distillation. Yet on the one hand, these quantities have to be purified with additional effort, while on the other hand, the residue is so viscous that it is difficult to empty the distillation boiler. With approximately 500 ppm the residue is practically catalyst-free and can be burned without any special precautions.

Other features of the invention will become apparent during the course of the following description of exemplary embodiments which are given for illustration of the invention and are not intended to be limiting thereof.

EXAMPLES

Example 1

Technical dicyclopentenol 132 g (1.0 mol) having 93% (gas chromatographic) content of pure dicyclopentadiende content are mixed with 120 g (2.0 mol) glacial acetic acid. After adding 2 g of (0.01 mol) BF₃·2 CH₃COOH, the reaction mixture is heated to reflux for one hour with stirring; thereby the temperature rises from initially 118° C. to 140° C. The reaction mixture is then distilled to yield the following:

(1) $Kp_{75}=58°$ C.; 66g (acetic acid)
(2) $Kp_{15}=\leqq 124°$ C.; 14 g (BF₃·2 acetic acid; acetic acid, dicyclopentenol acetate)
(3) $Kp_{15}=126°$ C.; 140 g (dicyclopentenol acetate)
(4) 31 g (residue) with C 80.3; H 8.7; 0 10.6; F 700 ppm Fraction )3) is passed through a 60 cm long and 2 cm wide column charged with marble/activated charcoal. Thereafter, 140 g of a product is obtained containing 78.4% of pure dicyclopentadiene with $nD^{20}32$ 1.4980, an acid value SZ - 0.24 and with 98.9% purity GC.

Example 2

Fraction (1) and fraction (2) from Example 1 are mixed with 54 g of acetic acid and 0.5 g of BF₃·2 CH₃COOH, and undergo a reaction analogous to Example 1, with worked up.

The yield is 146 g, corresponding to 81.8% dicyclopentenol acetate having the same data as noted in Example 1.

Example 3

With the addition of 1.2 g (0.01 mol) BF₃·O(CH₃)₂ as in Example 1, 132 g (1.0 mol) technical dicyclopentadiene are added to 148 g (2.0 mol) propionic acid and worked up.

(1) $Kp=85°$ C.; 91 g (propionic acid)
(2) $Kp_{15}=\geqq 138°$ C.; 15 g (BF₃ addition compound and transitions)
(3) $Kp_{15}=140°$ C.; 143 g (dicyclopentenol propionate)
(4) 28 g (residue) with C 81.28; H 8.92; 0 7.90; F 800 ppm Following purification over marble/activated charcoal, 143 g corresponding to 74.6% with $nD^{20}=1.4942$, acid value =0.16, and 99.2% purity are obtained.

Example 4

Analogous to Example 2, the pre-fractions from Example 3 are used in a recycling test.

The yield is 163 g, corresponding to 85.0% dicyclopentenol propionate with the same quality as in Example 3.

Example 5

Technical dicyclopentadiene 264 g (2.0 mol) having a 93% pure (gas chromatographic) dicyclopentadiene content are added to 0.62 g (0.01 mol) BF₃·O(CH₃)₂ and heated to 130° C. Under stirring 122 g (1.0 mol) benzoic acid are then added portion-by-portion during one hour. Thereby the reaction temperature rises to 155° C. This temperature is maintained one hour for the after-reaction, then left to cool. For work-up is distilled in vacuum.

(1) $Kp_3=50$ to 115° C.; 90 g (BF₃·O(CH₃)₂; DCP)
(2) $Kp_4=\leqq 180°$ C.; 27 g (benzoic acid; DCP benzoate)
(3) $Kp_4=182°$ C.; 200 g (DCP benzoate)
(4) 50 g (residue)

At $Kp_1=150°$ C., fraction 3) can be redistilled with practically no residue as a light yellow, readily oily liquid with $nD^{20}=1.5573$, an acid value SZ=0.1 and with 92.4% purity GC.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A process for the preparation of a dicyclopentenol ester of the formula:

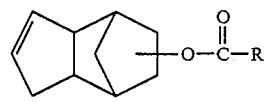

wherein:
R is a $C_{1-12}$ linear, branched or cyclic alkyl group, or R is a $C_{6-12}$ aryl group or a $C_{6-12}$ aryl group substituted by at least one member selected from the group consisting of halogen atoms and $C_{1-3}$ alkyl groups; said process comprising:
(i) reacting together dicyclopentadiene and an organic carboxylic acid in the presence of a catalyst, wherein said organic carboxylic acid has the formula:

and wherein said catalyst comprises at least one addition compound of $BF_3$; and (ii) obtaining said dicyclopentenol ester.

2. The process of claim 1, wherein said addition compound of $BF_3$ is a $C_{2-3}$ carboxylic acid addition compound of $BF_3$.

3. The process of claim 1, wherein said addition compound of $BF3$ is a methanol addition compound of $BF_3$ or an ethanol addition compound of $BF_3$.

4. The process of claim 1, wherein said addition compound of $BF_3$ is (1) a dimethyl ether addition compound of $BF_3$, (2) a diethyl ether addition compound of $BF_3$, or (3) a methyl ether ester addition compound of $BF_3$.

5. A process for the preparation of a dicyclopentenol ester of the formula:

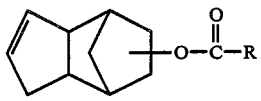

wherein:
R is a $C_{1-12}$ linear, branched or cyclic alkyl group, or R is a $C_{1-12}$ aryl group or a $C_{1-12}$ aryl group substituted by at least one member selected from the group consisting of halogen atoms and $C_{1-3}$ alkyl groups; said process comprising:

(i) reacting dicyclopentadiene with an organic carboxylic acid in the presence of a catalyst, wherein said organic carboxylic acid has the formula:

R—CO—OH and wherein said catalyst comprises an addition compound of $BF_3$;

(ii) isolating, separately, said addition compound of $BF_3$ and said dicyclopentenol ester from the reaction mixture; and (iii) using said isolated addition compound of $BF_3$ as the catalyst in a subsequent reaction of dicyclopentadiene with said organic carboxylic acid to produce said dicyclopentenol ester.

6. The process of claim 5, wherein said addition compound of $BF_3$ is a $C_{2-3}$ carboxylic acid addition compound of $BF_3$.

7. The process of claim 5, wherein said addition compound of $BF_3$ is a methanol addition compound of $BF_3$ or an ethanol addition compound of $BF_3$.

8. The process of claim 5, wherein said addition compound of $BF_3$ is (1) a dimethyl ether addition compound of $BF3$, (2) a diethyl ether addition compound of $BF_3$, or (3) a methyl ethyl ether addition compound of $BF_3$.

* * * * *